(12) United States Patent
Masuta et al.

(10) Patent No.: US 7,632,676 B2
(45) Date of Patent: Dec. 15, 2009

(54) PLANT VIRUS VECTOR

(75) Inventors: Chikara Masuta, Hokkaido (JP); Takeshi Matsumura, Hokkaido (JP); Noriko Itchoda, Hokkaido (JP)

(73) Assignees: National Institute of Advanced Industrial Science and Technology, Tokyo (JP); Hokuren Federation of Agricultural Cooperatives, Sapporo-shi (JP); National University Corporation Hokkaido University, Sapporo-shi (JP)

( * ) Notice: Subject to any disclaimer, the term of this patent is extended or adjusted under 35 U.S.C. 154(b) by 237 days.

(21) Appl. No.: 10/562,227

(22) PCT Filed: Jun. 25, 2004

(86) PCT No.: PCT/JP2004/009035

§ 371 (c)(1), (2), (4) Date: Jun. 5, 2006

(87) PCT Pub. No.: WO2005/001102

PCT Pub. Date: Jan. 6, 2005

(65) Prior Publication Data

US 2007/0143877 A1    Jun. 21, 2007

(30) Foreign Application Priority Data

Jun. 27, 2003    (JP)    ............................. 2003-185981

(51) Int. Cl.
C12N 15/00    (2006.01)
A01H 1/00    (2006.01)
C12N 15/82    (2006.01)
C12N 15/87    (2006.01)

(52) U.S. Cl. ..................... 435/320.1; 800/280; 800/278

(58) Field of Classification Search ........................ None
See application file for complete search history.

(56) References Cited

OTHER PUBLICATIONS

Chen et al. 2007, Virus Genes 35:405-413.*
Ding et al. 1996, PNAS, 93:7470-7474.*
Soards et al. 2002, MPMI 15:647-653.*
Roossinck et al. 1999, J. of Virology 73:6752-6758.*
Ding et al. 1995, EMBO 5762-5772.*
Ding, Shou-Wei et al., "An interspecies hybrid RNA virus is significantly more virulent than either parental virus", Proc. Natl. Acad. Sci, vol. 93, pp. 7470-7474, 1996.
Shi, Bu-Jun et al., "Differential Virulence by Strains of Cucumber mosaic virus is Mediated by the 2 b Gene", Molecular Plant-Microbe Interactions, vol. 15, No. 9, pp. 947-955, 2002.
Ding, Shou-Wei et al., "A novel naturally occurring hybrid gene encoded by a plant RNA virus facilitates long distance virus movement", The EMBO Journal, vol. 14, No. 23, pp. 5762-5772, 1995.
Soards, Avril J. et al., "Virulence and Differential Local and Systemic Spread of Cucumber mosaic virus in Tobacco are Affected by the CMV 2b Protein", Molecular Plant-Microbe Interactions, vol. 15, No. 7, pp. 647-653, 2002.
Zhao, Y. et al, "Development and evaluation of a complementation-dependent gene delivery system based on Cucumber mosaic virus", Archives of Virology, vol. 145, No. 11, pp. 2285-2295, 2000.
Canto, Tomas et al, Characterization of Cucumber Mosaic Virus. IV., Movement Protein and Coat Protein are both essential for cell-to-cell movement of cucumber mosaic virus, Virology, vol. 237, No. 2, pp. 237-248, 1997.
Sugiyama, Yoshinori et al., "Systemic production of foreign peptides on the particle surface of Tobacco mosaic virus", FEBS Letters, vol. 359, pp. 247-250, 1995.
Fernandez-Fernandez, M. Rosario et al., "Development of an antigen presentation system based on plum pox potyvirus", FEBS Letters, vol. 427, pp. 229-235, 1998.
Donson, J. et al., "Systemic expression of a bacterial gene by a tobacco mosaic virus-based vector", Proc. Natl. Acad. Sci, vol. 88, pp. 7204-7208, 1991.
Mori, Masashi et al., "mRNA amplification system by viral replicase in transgenic plants", FEBS Letters, vol. 336, No. 1, pp. 171-174, 1993.
Shi, Bu-Jun, et al.,"The 2b Protein of Cucumoviruses Has a Role in Promoting the Cell-to-cell Movement Of Pseudorecombinant Viruses", Molecular Plant-Microbe Interactions, vol. 16, No. 3, pp. 261-267, 2003.

* cited by examiner

Primary Examiner—Ashwin Mehta
Assistant Examiner—Li Zheng
(74) Attorney, Agent, or Firm—Oblon, Spivak, McClelland, Maier & Neustadt, L.L.P.

(57) ABSTRACT

A novel plant virus vector and a method of gene expression into plants are provided, and the present invention relates to a plant virus vector characterized in that a part of the sequence of the 2b region of the RNA2 molecule of the Cucumber mosaic virus (CMV) is deleted; the aforementioned plant virus vector characterized in that the region from the StuI site to the stop codon of the 2b ORF of pCY2, which is an infectious clone of CMV-Y RNA2, is deleted; and a method of gene expression in plants characterized in that a foreign gene is introduced so as to be stably expressed in a plant using the genetic recombinant. This vector is useful as a plant RNA vector for causing stable expression of foreign genes.

4 Claims, 4 Drawing Sheets

PLANT VIRUS VECTOR

TECHNICAL FIELD

The present invention relates to a plant RNA virus vector, and relates more particularly to a novel plant virus vector in which the RNA2 molecule of a cucumber mosaic virus (CMV) having a viral genome comprising four segments RNA1, RNA2, RNA3A and RNA3B is altered, and to a method of gene expression in plants.

In the field of plant gene manipulation and gene expression methods, the present invention is useful because it provides a novel plant RNA virus vector, which can be used as a vector, which has more than 1000 species of plant hosts, and can stably express foreign genes, and a novel method of gene expression in plants.

BACKGROUND ART

Conventionally, many researches into plant RNA virus vectors have been performed by using the infectious clones of the tobacco mosaic virus (TMV) and bromo mosaic virus (BMV), which have extremely strong proliferation potency in infected plants. Several systems for expressing foreign genes have also been developed in this field based on differences in the expression patterns of viral genes and the like. In the case of TMV and Potyviruses, for example, vectors have been developed, which express proteins by means of a viral CP gene fused to a foreign gene (Sugiyama, Y., Hamamoto, H., Takemoto, S., Watanabe, Y. and Okada, Y., "Systemic production of foreign peptides on the particle surface of Tobacco mosaic virus," *FEBS Letters* 359, 247-250 (1995); Fernandez-Fernandez, M. R., Martinez-Torrecuadrada, J. L., Casal, J. I. and Garcia, J. A., "Development of an antigen presentation system based on plum pox potyvirus," *FEBS Letters* 427, 229-235 (1998)). A vector expressing a foreign gene via the subgenome by introducing a subgenomic promoter of Odontoglossum ringspot virus, a close relative of TMV has also been developed (Donson et al., "Systemic expression of a bacterial gene by a tobacco mosaic virus-based vector," *Proc. Natl. Acad. Sci. USA* 88: 7204-7208 (1991)).

However, these viruses were developed using rod-shaped and string-shaped viruses, typically TMV and Potyviruses. The advantage of rod-shaped and string-shaped viruses is that they present fewer physical limitations than spherical viruses on the length of the foreign gene to be inserted. On the other hand, as an expression vector system using the spherical virus BMV, a method of inoculating tobacco expressing 1a protein and 2a protein replicase genes with RNA3 having a foreign gene has been reported (Mori, M., Kaido, M., Okuno, T. and Furusawa, I., "mRNA amplification system by viral replicase in transgenic plants," *FEBS Lett.* 336, 171-174 (1993).

Several studies have also been done on CMV viral vectors. One of these involves the development of a 4-segment CMV vector by means of complementation (see Zhao, Y., Hammond, J., Tousignant, M. E. and Hammond, R. W., "Development and evaluation of a complementation-dependent gene delivery system based on Cucumber mosaic virus," *Archives of Virology* 145, 2285-2295 (2000)). MP and CP are coded for the RNA3 of CMV, and both MP and CP are essential for intercellular movement of viruses (see Zhao et al., above). These inventors have already altered the RNA3 molecule to construct RNA3A (in which the MP region is replaced by the GFP gene) and RNA3B (which lacks the CP gene), and have developed a virus vector that moves between cells by means of complementation. When this was used as CMV having a 4-segment genome (RNA1, RNA2, RNA3A and RNA3B) to inoculate *benthamiana*, GFP fluorescence was observed in a minor vein of the inoculated leaf. Moreover, when a multicloning site was inserted into the missing CP region of RNA3B, and the GUS (bacterial-β-glucuronidase) gene and BYMV (Bean yellow mosaic virus) CP gene were introduced therein, GUS activity and BYMV-CP were detected in a minor vein of the infected leaf. However, expression of the introduced genes was not observed in the upper leaf because RNA3A and RNA3B underwent homologous RNA recombination with each other.

Thus, although there have been various studies of CMV virus vectors, up till now in developing CMV vectors, the methods for introducing foreign genes into RNA3 have been adopted, with the result that proliferation has not been observed in the upper leaf in any case, and there is a strong need for improvement. In light of the prior art, the inventors attempted to introduce the foreign gene GFP into the RNA2 molecule of CMV with the aim of developing a novel virus vector, and perfected the present invention when they succeeded in developing a novel CMV vector in which the RNA2 molecule of CMV is altered.

DISCLOSURE OF THE INVENTION

That is, it is an object of the present invention to provide a novel CMV vector that exhibits systemic infection in inoculated plants, and has the function of stably expressing foreign genes.

It is also an object of the present invention to provide a novel plant virus vector that has about 1000 or more plant hosts in which it can be used favorably as a vector.

Moreover, it is an object of the present invention to provide a CMV vector capable of causing stable expression of an introduced foreign gene along with a novel method of expressing plant genes using this vector.

To resolve the aforementioned problems, the present invention comprises the following technical means.

(1) A plant virus vector characterized in that a part of the sequence of the 2b region of the RNA2 molecule of the Cucumber mosaic virus (CMV) is deleted, and a foreign gene introduction site is introduced into the part of the sequence.

(2) The plant virus vector according to (1) above, wherein the region from the StuI site to the stop codon of the 2b ORF of pCY2, which is an infectious clone of CMV-Y RNA2, is deleted.

(3) The plant virus vector according to (2) above, wherein a point mutation which changes the 8th U (uracil) of the 2b ORF to A (adenine) is introduced.

(4) The plant virus vector according to (2) above, wherein a region comprising StuI-stop-MluI-SnaBI is introduced into the StuI-AvrII region of pCY2.

(5) The plant virus vector according to (1) above, wherein the CMV is a CMV isolate belonging to subgroup 1 or subgroup 2, such as CMV-Y, SSV, CMV-O, CMV-L, m2-CMV or HL-CMV.

(6) A genet recombinant characterized in that a foreign gene is introduced into the StuI site and MluI region of the plant virus vector defined in (4) above.

(7) A method of gene expression in plants characterized in that a foreign gene is introduced so as to be stably expressed in a plant using the recombinant defined in (6) above.

Next, the present invention is explained in more detail.

The present invention relates to a novel CMV vector, wherein a part of the sequence of the 2b region of the RNA2 molecule of a 4-segment virus genome consisting of segments RNA1, RNA2, RNA3A and RNA3B of the Cucumber mosaic virus (CMV) is deleted, and a foreign gene introduction site is inserted into the part of the sequence. As explained in detail in the examples below, an example of a plant virus vector of the present invention is a plasmid (named as pCY2-2bΔStu) in which the region from the StuI site to the stop codon of the 2b ORF of pCY2, which is an infectious clone of CMV-Y RNA2 is deleted. As a specific example of a method of preparing this, a method wherein the 3' end nontranslated region immediately after the 2b ORF of pCY2, which is an infectious clone of CMV-Y RNA2, is subjected to PCR using the primer Y2b-Stu and the 3' end primer CMV-DET-3-340, which are described in the following examples, and a region comprising StuI-stop-MluI-SnaBI is introduced into the StuI-AvrII region of pCY2 is exemplified.

In CMV-Y RNA2, the 2b protein is coded for in overlapping fashion with the 2a protein, which forms part of the virus's multiple enzyme complex. Consequently, a stop codon is introduced into the ORF of the 2b protein to create a virus that does not express the CMV-Y 2b protein. When introducing a stop codon into the 2b protein ORF, it is needed that amino acid substitutions cannot be allowed to occur in the 2a protein. As an example of a method that fulfills these conditions, one in which a point mutation is introduced which changes the $8^{th}$ base of the 2b ORF from U (uracil) to A (adenine) is exemplified.

Specifically, in the sequence into which the point mutation is to be introduced, the sense and antisense primers described in the examples below are prepared, and amplified by PCR together with the respective 3' and 5' primers, the respective bands are cut out, mixed and used as templates in PCR using for example the 5' and 3' primers described in the examples below, the PCR fragments are cleaved with HindIII and BlnI, and the resulting fragments are cloned into the HindIII-XbaI region of pUC119. The HindIII-StuI region is cut from the pUC119-point mutation and the HindIII-StuI region of pCY2 is introduced to construct pCY2-2b stop having a point mutation introduced as a stop codon into the 2b ORF.

By these methods, a CMV-Y 2b protein C-end deletion virus vector can be prepared, which is a virus vector that does not express the 2b protein. As shown in the examples below, this modified vector produced systemic infection in a plant inoculation test, but with slower development of symptoms than the CMV-Y wild type. In the present invention, it is possible to cause a stable expression of a foreign gene in a plant by introducing the foreign gene into the StuI site and MluI region of the aforementioned modified CMV-Y virus vector, and inflecting this to a plant body.

The CMV vector of the present invention is capable of producing stable expression of GFP for example in the first generation inoculated with an RNA transcription product from PCY2-GFP with green fluorescent protein (GFP) incorporated therein. Successful GFP expression in *benthamiana* upper leaves is attributed to the fact that the intermolecular recombination between segments which occurred with the aforementioned 4-segment CMV vectors did not occur here because the foreign gene was introduced directly into the RNA2 molecule. Even when SSV (Soybean stunt virus, a strain of CMV) was used in place of CMV-Y, expression of GFP was seen in the upper leaves of *benthamiana*, so application to soy beans can be reasonably expected.

In the system of the present invention, in order to avoid such template switching, it is possible for example to change bases without altering the amino acids of GFP, or to modify the 3' end sequence of CMV-Y to the 3' end of another CMV strain such as SSV or HL-CMV (lily strain). Although not limited thereby, the vector of the present invention may preferably be pCY2-2bΔStu (2980 bases) in which the 71 bases at the 3' end of 2b have been deleted from the 3051 bases of CMV-Y RNA2.

As mentioned above, rod-shaped and string-shaped viruses such as tobacco mosaic virus have been conventionally used in developing RNA virus vectors. The advantage of rod-shaped and string-shaped viruses is that they present fewer physical limitations than spherical viruses on the length of the foreign genes that can be inserted. On the other hand, spherical viruses such as the one used in the present invention are difficult to use as virus vectors because of their particle shape, and while methods have been adopted of developing 4-segment CMV vectors by complementation and introducing foreign genes into RNA3, proliferation has not occurred in the upper leaves of the inoculated plant. In the present invention, a novel CMV vector has been developed in which the RNA2 molecule of CMV has been modified. CMV isolates belonging to CMV subgroups 1 and 2, such as CMV-Y, CMV-O, CMV-L, SSV and m2-CMV, can be used as CMV.

In the present invention, systemic infection of the inoculated plant body and stable expression of GFP were confirmed from an analysis of functional characteristics using *Nicotiana benthamiana* as the host plant and the GFP gene as the foreign gene in this CMV vector, but the present invention is not limited thereby and is applicable to appropriate plants such as tomatoes, tobacco, spinach, soy beans, cucumbers, potatoes and the like and to foreign genes up to about 1000 bp in length. The present invention is useful in that it provides a novel CMV vector having about 1000 or more species of host plants in which it can be used as a vector and in which it can stably express foreign genes. Moreover, because RNA2 is modified this vector is useful because it offers the novel property of allowing the induction of silencing, which has not been observed previously in CMV.

The present invention can exhibits the following effects: (1) it proves a novel plant RNA virus vector, (2) which exhibits systemic infection in inoculated plants and can produce stable expression of a foreign gene, (3) which has about 1000 or more species of plants as hosts in which it can be used as a vector, (4) it proves a new plant gene expression method, (5) which is useful as a new plant gene expression method for introducing foreign genes and causing them to be expressed stably in plants, and (6) which is highly replicable and effective for stopping gene expression by gene silencing.

BEST MODE FOR CARRYING OUT THE INVENTION

Figure 1:
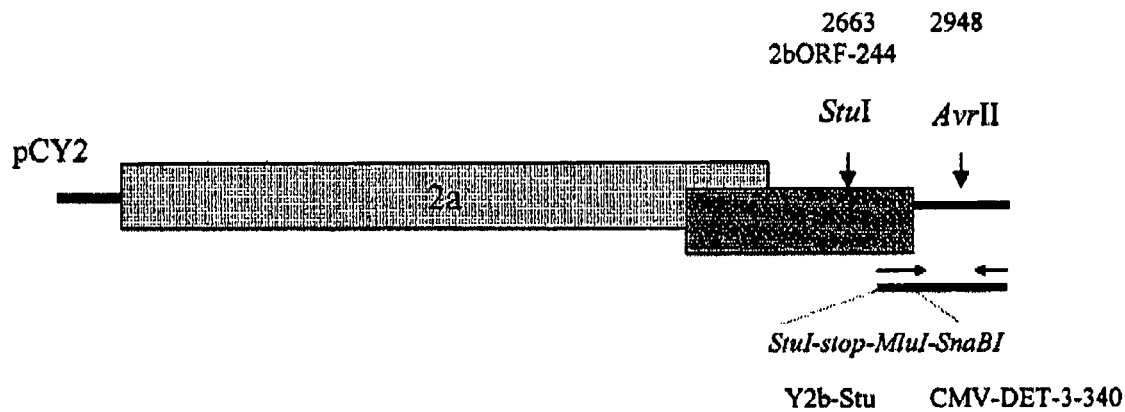
FIG. 1 is a structural diagram of pCY2-2bΔStu, and contains the primers Y2b-Stu: CGAGGCCTGACGCGTG-TACGTAAACCTCCCCTTCCGCATC (SEQ ID NO: 1); and CMV-DET-3-340: CCATCGATTGGTCTCCTTTTGGAG-GCC (SEQ ID NO: 2).
Figure 1:
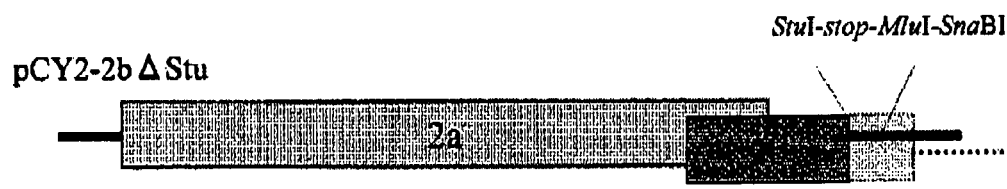

The present invention is explained in detail below using examples, but the present invention is not in any way limited by the following examples

EXAMPLES (1) Test Virus

The CMV-Y strain of CMV was used as the test virus, and was subcultured in *Nicotiana Benthamiana* or tabaco (*Nicotiana tabacum*) in the Greenhouse For Forced Regeneration of Plants belonging to the research course of the science of agriculture at the postgraduate course, Hokkaido University (air temperature 20 to 30° C., natural daylight in Sapporo).

(2) Growing of Test Plants

The *Nicotiana Benthamiana* and *Nicotiana tabacum* were grown by the following methods.

4 pots were filled with planting soil (4 shovels of Takii soil (Takii Seed Co.), 4 shovels of Sankyo cultivation soil (Sankyo), 1 shovel of black dirt), a handful of vermiculate (Showa vermiculate, autoclaved) was scattered on top, the soil was adequately watered and about 40 seeds were planted therein. These were grown in the Greenhouse For Forced Regeneration of Plants belonging to the research course of the science of agriculture at the postgraduate course, Hokkaido University (air temperature 28° C., 16 hours daylight) while being culled from time to time so that the growth stages of the plants would be uniform. Once they had reached 2 to 3 cm, they were transplanted 2 by 2 at a time to transplantation soil (2 shovels of Takii soil, 3 shovels of Sankyo cultivation soil, 1 shovel of black dirt, 1 shovel of leaf mould (Sapporo Iseki Hanbai)). 1 week after the transplantation they were covered with newspaper to block the sunlight, and subsequently fertilized in accordance with the growth of the plant bodies.

(3) Inoculation Test

The *Nicotiana Benthamiana* and *tabacum* plants which had developed 3 to 5 leaves about 1 to 2 weeks after the transplantation had high sensitivity to viruses and were the most suited to inoculation.

The upper leaves of *benthamiana*, which exhibit viral symptoms such as mosaic and rugose, were used as the inoculum source. All of the leaves to be inoculated in plants that had reached the inoculation stage were thinly sprinkled with carborundum (Nacalai-mesh 600-hot air sterilized). DIECA (N,N sodium diethyldithiocarbamate, Wako, added immediately before inoculation) was added to a final concentration of 10 mM to 1 ml of the following 0.1 M phosphate buffer (pH 7.1), and ground in a mortar together with 0.1 g of infected leaves as the inoculum source. The raw ground liquid was put on a fingerstall and applied with a light patting action to the leaf surfaces. The plants were watered immediately after inoculation to wash the raw liquid and carborundum from the leaf surfaces, and were left covered with newspaper to shield them from light until the next day.

The 0.1 M phosphate buffer (pH 7.1) was prepared by mixing 33 ml of 0.2 M phosphoric acid-sodium solution (Nacalai) with 67 ml of 0.2 M disodium phosphate solution (Nacalai) to a pH of 7.1, adjusting the volume with distilled water and autoclaving for a total of 200 ml.

(4) Preparation of Competent Cells

*E. coli* strain JM109 (TaKaRa) was added to 2 ml of the following SOB liquid medium, and shaking cultured for 12 to 14 hours at 37° C. 50 ml of SOB liquid medium was seeded with 0.5 ml of the previous culture liquid, and shaking cultured for about an hour and a half at 37° C. ($OD_{550}$=0.4 to 0.8). After being left on ice for 10 minutes, this was transferred to a Nalgene tube, and centrifuged for 10 minutes at 4° C., 3500 rpm. After removal of the supernatant, it was gently suspended in 17 ml of the following ice-cooled TFB. After being left for 20 minutes on ice, it was centrifuged again for 10 minutes at 4° C., 3500 rpm. The supernatant was discarded, 2 ml of ice-cooled TFB was added thereto, and the precipitate was gently suspended on the surface of the liquid. This was left for 30 minutes on ice, 150 μl of DMSO (dimethyl sulfoxide, Nacalai) was added slowly drop by drop, and this was left for a further 10 minutes on ice. 100 μl each was dispensed into Eppendorf tubes using a chip with the tip cut off, and stored at −80° C.

The SOB liquid medium was prepared by mixing 10 ml of Bacto™ Tryptone (Becton Dickinson) 20 g:Bacto™ Yeast Extract (Becton Dickinson) 5 g:1M NaCl solution with 2.5 ml of 1M KCl solution, adjusting the amount to 1 L with distilled water, autoclaving, and adding 1/100 that amount of filter sterilized 1M $MgCl_2$ solution (Nacalai) and 1 M $MgSO_4$ solution (Nacalai) before use.

The TFB (transformation buffer) was prepared with a composition of 35 mM potassium acetate (Nacalai), 50 mM $CaCl_2$ (Wako), 45 mM $MnCl_2$ (Nacalai), 100 mM RbCl (Nacalai), and 15% sucrose (Wako)-acetic acid (Wako) to a pH of 5.8, and filter sterilized.

(5) Transformation

1 μl of plasmid (about 5 μl in the case of a ligation reaction liquid) was added to 100 μl of gently dissolved competent cells, and left for 30 minutes on ice to mix by natural diffusion. This was placed for 45 seconds in a 42° C. water bath and immediately ice cooled to introduce the plasmid into the *E. coli*. 0.9 ml of the following 2YT liquid medium was added along the walls of the tube, stationary cultured for 30 minutes at 37° C., and then shaking cultured for 30 minutes at 37° C. 100 μl of this was spread on the following LB-amp medium. For purposes of blue/white selection, 50 μl of 2% X-gal (5-bromo-4-chloro-3-indryl-β-D-galactopyranoside (Wako) dissolved to a 2% concentration in N,N-dimethylformamide (Nacalai)) and 10 μl of 100 mM IPTG (isopropyl-β-D(−)-thiogalactopyranoside solution (Wako) and filter sterilized) were applied to LB medium, and 100 μl of *E. coli* culture liquid was spread thereon. This was cultured for 12 to 16 hours at 37° in an incubator in reverse.

The 2YT liquid medium was prepared by mixing 16 g of Bacto™ Tryptone, 10 g of yeast extract and 10 g of NaCl, adjusting the amount of 1 L with distilled water and autoclaving.

The LB-amp medium was prepared by mixing 10 g of Bacto™ Tryptone, 5 g of yeast extract, 10 g of NaCl and 15 g of agar (Wako), adjusting the amount to 1 L with distilled water, autoclaving, cooling to about 50° C., adding about 1/1000 the amount of 50 mg/ml ampicillin stock (Wako, filter sterilized), and dispensing into sterilized Petri dishes before solidification.

(6) Plasmid Extraction

The *E. coli* colonies obtained by transformation were transferred with sterilized toothpicks into 2 ml of 2YT liquid medium with 2 μl of 50 mg/ml ampicillin stock added, and shaking cultured for 12 to 14 hours at 37° C. This culture liquid was placed in a 1.5 ml tube and centrifuged for 1 minute at 10,000 rpm. The supernatant was removed with an aspirator, and 200 μl of the following Solution 1 was added to each tube and completely suspended with a tube mixer. 200 μl of the following Solution 2 was then added to each and mixed by inverting. Next, 200 µl of the following Solution 3 was added to each and again mixed by inverting. This was centrifuged at 14,000 rpm at 4° C. for 10 minutes, and the supernatant was transferred to a tube and centrifuged again (14,000 rpm, 5 minutes) to completely remove the protein. The supernatant was collected and an equal amount of isopropyl alcohol (Wako) was added thereto and mixed by inverting. This was centrifuged for 5 minutes at 14,000 rpm, and the supernatant was discarded. 500 µl of 80% ethanol (Nacalai) was added and centrifuged for 5 minutes at 14,000 rpm, and the supernatant was discarded. 100 µl of RNaseA diluted with TE (10 mM Tris-Hcl (pH 7.5), 1 mM EDTA (pH 8.0)) to a final concentration of 2 µg/ml was added to each, lightly mixed, and left for 30 minutes at 37° C. 60 µl of the following Solution 4 was added to this, agitated in a vortex mixer, and left for 45 minutes on ice. After 10 minutes of centrifugation at 14,000 rpm, the supernatant was discarded. 500 µl of 80% ethanol was added and centrifuged for 5 minutes at 14,000 rpm. The supernatant was discarded, and the remainder was dried under reduced pressure for 5 to 10 minutes and suspended in 30 µl of sterilized water. This plasmid sample was stored at −30° C.

a) Solution 1

25 mM Tris (2-amino-2-hydroxymethyl-1,3-propanediol, Wako)-HCl (pH 8.0), 10 mM EDTA (ethylenediamine-N,N, N',N'-tetraacetic acid, Dojin Chemical), 50 mM glucose (Wako)

b) Solution 2

0.2 N NaOH (Wako), 1% SDS (sodium lauryl sulfate, Nacalai)

c) Solution 3

60 ml 5 M potassium acetate solution, 11.5 ml acetic acid, 28.5 ml distilled water d) Solution 4

20% PEG #6000 (polyethylene glycol, Nacalai), 2.5 M NaCl (7) Basic Gene Manipulation Methods 1) Restriction Enzyme Treatment Left for 1 hour or more at the specified temperature in a 20 µl reaction system using 0.5 µl of each manufacturer's restriction enzyme with the attached buffers.

2) Electrophoresis

Electrophoresis was performed with TBE as the electrophoresis buffer using a TBE (89 mM Tris-base, 89 mM boric acid (Wako), 2 mM EDTA) agarose (Gene Pure™ LE AGAROSE-BM) gel at a concentration suited to the length of the target DNA. Following electrophoresis, the gel was stained with ethidium bromide solution (final concentration 0.5 µg/ml).

3) Phenol/chloroform Extraction

Sterile water was added to the sample DNA liquid to a total of 100 µl, and 50 µl of TE saturated phenol (Nippon Gene) and 50 µl of chloroform (Wako) were added and agitated for 1 to 2 minutes in a tube mixer to inactivate the protein. After 5 minutes of centrifugation at 14,000 rpm, the water layer alone was transferred to a 1.5 ml tube. 100 µl of chloroform was added, followed by centrifugation for 5 minutes at 14,000 rpm in a vortex mixer. The water layer alone was transferred to a 1.5 ml tube.

4) Ethanol Sedimentation

10 µl of 3 M sodium acetate (Nippon Gene), 330 µl of 100% ethanol and 1 µl of Ethachin Mate (Nippon Gene) were added to 100 µl of sample DNA liquid and agitated, followed by 10 minutes of centrifugation at 14,000 rpm and removal of the supernatant. 500 µl of 80% ethanol was added and centrifuged for 2 to 3 minutes t 14,000 rpm. This was dried under reduced pressure after removal of the supernatant.

5) Cloning

SeaKem™ GTC™ agarose (BMA) was used to collect DNA from the gel, and electrophoresis was performed using agarose gel with EtBr added directly to a final concentration of 0.5 µg/ml. The gel section containing the desired band was cut out and DNA was collected using a QIAEX™ II Gel Extraction Kit 150 (QIAGEN). The collected DNA solution was phenol/chloroform extracted, precipitated with ethanol, and suspended in 5 µl of sterile water. A DNA Ligation Kit Ver. 2 (TaKaRa) was used for ligation of the vector and insert. An amount of Ver. 2-I liquid equal to the amount of collected DNA solution was added and suspended. This was left for 30 minutes at 16° C., after which half of the ligation reaction liquid was transformed into competent cells of E. coli.

(8) In vitro Transcription of Infectious Clone

4 µl of the infectious clone extracted by alkali-SDS was linearized with the restriction enzyme used for run-off transcription, phenol/chloroform extracted and ethanol precipitated, and the resulting pellets were suspended in 9 µl of sterile water. The transcription reaction liquid was mixed as follows.

TABLE 1

| (Transcription reaction liquid) | |
|---|---|
| Template solution | 9 µl |
| 0.1 M DTT | 5 µl |
| 10 × T7 RNA polymerase Buffer*[11] | 2 µl |
| 10 mM m$^7$ G(5')ppp(5')G RNA Capping Analog (Invitrogen) | 2 µl |
| 20 × NTP mixed liquid*[12] | 1 µl |
| RNase inhibitor*[13] | 0.5 µl |
| T7 RNA polymerase | 0.5 µl |

*[11]Included with T7 RNA polymerase (TaKaRa)
*[12]20 × NTP (1 mM ATP, 1 mM CTP, 1 mM UTP, 0.1 mM GTP-Roche)
*[13]Ribonuclease inhibitor, recombinant, solution (Wako)

This was left for 1 hour at 37° C. A further 0.5 µl of T7 RNA polymerase was then added to the transcription reaction liquid, which was left for another hour at 37° C. When inoculation was not immediate, the transcription product was stored at −80° C. 15 µl of each of the transcription products (RNA 1, 2 and 3) was mixed with 30 µl of 0.1 M phosphate buffer (PH 7.1). 12.5 µl of each transcription inoculation liquid per *benthamiana* plant was inoculated using carborundum and a fingerstall as in ordinary virus inoculation.

(9) RNA Extraction (Phenol-SDS)

0.1 g of sample (or protoplast) was ground with 500 µl of RNA extraction buffer and 500 µl of TE saturated phenol, and transferred to a 1.5 ml tube. After about 20 seconds in a vortex mixer, this was cool centrifuged for 5 minutes at 14,000 rpm. The supernatant (water layer) was transferred to a separate tube, an amount of phenol/chloroform (1:1) equal to the amount of supernatant was added, and after being vigorously agitated in a vortex mixture this was cool centrifuged for 5 minutes at 14,000 rpm. The supernatant was transferred to a separate tube, and extracted repeatedly with phenol/chloroform until the white protein layer disappeared. After a final rinsing with an equal amount of phenol/chloroform, the water layer was separated out, and ¹⁄₁₀ the amount of 3 M sodium acetate and 3 times the amount of 100% ethanol were added thereto. After vortex mixing, this was cool centrifuged for 5 minutes at 14,000 rpm. The supernatant was discarded, and 500 μl of 80% ethanol was added and cool centrifuged for 5 minutes at 14,000 rpm. After being dried under reduced pressure for 5 to 10 minutes this was suspended in 50 μl of sterile water for RNA (10 μl for protoplasts), and centrifuged for about 1 minute at 14,000 rpm. When precipitation occurred, the supernatant alone was transferred to a separate tube. The RNA extraction buffer was composed of 25 mM Tris-Hcl (pH 7.5), 25 mM $MgC_{12}$, 25 mM KCl and 1% SDS.

(10) RT-PCR

1) Reverse Transcription Reaction

The following reaction solution was prepared

TABLE 2

| | |
|---|---|
| RNase Free $dH_2O$*[15] | 7.5 μl |
| 25 mM $MgCl^{2+}$*[15] | 4 μl |
| each 10 mM dNTP Mixture*[15] | 2 μl |
| 10 × RNA PCR Buffer*[15] | 2 μl |
| RNase Inhibitor | 0.5 μl |
| 3' primer | 1 μl |
| Sample RNA | 2 μl |
| AMV Reverse Transcriptase XL (TaKaRa) | 0.5 μl |

*[15]Included with RNA PCR ™ kit (AMV) Ver. 2.1 (TaKaRa)

This was left for 1 hour at 45° C. It was then boiled for 5 minutes and rapidly cooled for 5 minutes to inactivate the reverse transcriptase.

2) PCR Reaction

A PCR mix was prepared as follows

TABLE 3

| | |
|---|---|
| Sterile water | 63.5 μl |
| 25 mM $MgCl_2$*[16] | 6 μl |
| 10 × LA PCR ™ BufferII ($Mg^{2+}$free)*[16] | 8 μl |
| 5' primer | 1 μl |
| 3' primer | 1 μl |

*[16]Included with TaKaRa LA Taq ™

20 μl of reverse transcription reaction liquid was added to this, followed by 0.5 μl of TaKaRa LA Taq™, and PCR was performed. The PCR product was electrophoresed on 1% agarose gel and amplification of the target fragment was confirmed.

(11) Sequencing 1.5 μl of distilled water was added to 1 μl of sample extracted by the alkali-SDS method to prepare a template DNA solution. A, C, G and T substrate solutions (Thermo sequence fluorescent labeled primer cycle sequencing kit with 7-deaza-dGTP (Amersham Pharmacia)) was added to 0.25 μl of M13 primer (IRD800 Infrared Dye Labeled Primer-M13 Forward (−29)/IRD800, M13 Reverse/IRD800-Nisseibo) to prepare 4 different primer-substrate solutions. 2.5 μl of template DNA solution and 1.25 μl of primer-substrate mixture solution was dispensed into an 8-strip PCR tube, and subjected to PCR under the following conditions.

TABLE 4

| (PCR conditions) | | |
|---|---|---|
| 95° C. | 5 minutes | 1 cycle |
| 95° C. | 30 seconds | |
| 50° C. | 30 seconds | 30 cycles |
| 70° C. | 1 minute | |
| 10° C. | ∞ | |

After the PCR reaction, 2 μl of loading dye fluorescent samples-Stop solution (Amersham) was added). The sequence gel solution was filtered with a 0.2 μm membrane, and deaerated for about 30 minutes. 400 μl of 10% APS (ammonium peroxydisulfate, Nacalai) and 40 μl of TEMED (N,N,N',N'-tetramethyl-ethylenediamine, Nacalai) were added to the gel solution, which was immediately poured into a gel plate and laid on a horizontal surface with a comb inserted. 30 minutes later the gel plate was wrapped together with water-wetted JK wiper (Crecia) at both ends, and left for 5 hours or more. The gel plate was set in a Li-cor Sequencer, 1 L of 1×TBE was poured into a specific position, and 1.8 μl of PCR sample was added to each well. Electrophoresis was performed for about 24 hours.

The sequence gel solution was mixed with 25.2 g of urea (Nacalai), 7.2 ml of 10×TBE and 4.8 ml of Long Ranger™ gel solution (BMA), and filled up to 60 ml with distilled water.

(12) Detection of GFP Fluorescence

A stereomicroscope (SZX-12, Olympus) was used in a dark room to detect GFP fluorescence in inoculated leaves and upper leaves that showed signs of infection.

(13) Preparation of CMV-Y 2b Protein C-end Deletion Virus

The 3' end nontranslated region directly after the 2b ORF of pCY2 (an infectious clone of CMV-Y RNA2) was subjected to PCR using the following primer Y2b-Stu and 3' end primer CMV-DET-3-340, and the StuI-AvrII region of the PCR product was introduced into the StuI-AvrII region of pCY2.

(Primers)

```
Y2b-Stu:
                               (SEQ ID NO: 1)
CGAGGCCTGACGCGTGTACGTAAACCTCCCCTTCCGCATC;

CMV-DET-3-340:
                               (SEQ ID NO: 2)
CCATCGATTGGTCTCCTTTTGGAGGCC;
```

A plasmid (pCY2-2bΔStu) was prepared having the region from the StuI site to the stop codon deleted from the 2b ORF of the CMV-Y RNA2 infectious clone pCY2. FIG. 1 is a structural diagram of pCY2-2bΔStu.

This pCY2-2bΔStu was in vitro translated, and used in *Nicotiana benthamiana* and *tabacum* inoculation tests together with the transcription products of pCY1 and pCY3. The results are shown in Table 5. Y1 Y2bΔSTu Y3 produced a strong mosaic in the upper leaves of *benthamiana*, but the symptoms progressed more slowly than those of the CMV-Y wild type, which produces strong mosaic and plant death. Mosaic symptoms also appeared in the upper leaves of *tabacum*, with systemic infection, but as in the case of *benthamiana* the symptoms progressed more slowly than those of CMV-Y.

TABLE 5

Inoculation tests of CMV-Y 2b modified virus in *Nicotiana benthamiana* and tobacco, comparison of symptoms

| | | | |
|---|---|---|---|
| Y1-Y2bΔStu-Y3 | +(M) | +(CS) | +(M) |
| Y1-Y2bstop-Y3 | +(M) | +(CS) | +(M) |
| CMV-Y | +++(M) | +++(CS) | +++(M) |

| Inoculated | *Benthamiana* | Tobacco | |
|---|---|---|---|
| Virus | Upper leaves | Inoculated leaves | Upper leaves |

M: Mosaic, CS: Chlorotic spot

(14) Preparation of Virus Not Expressing CMV-Y 2b Protein

Figure 2:
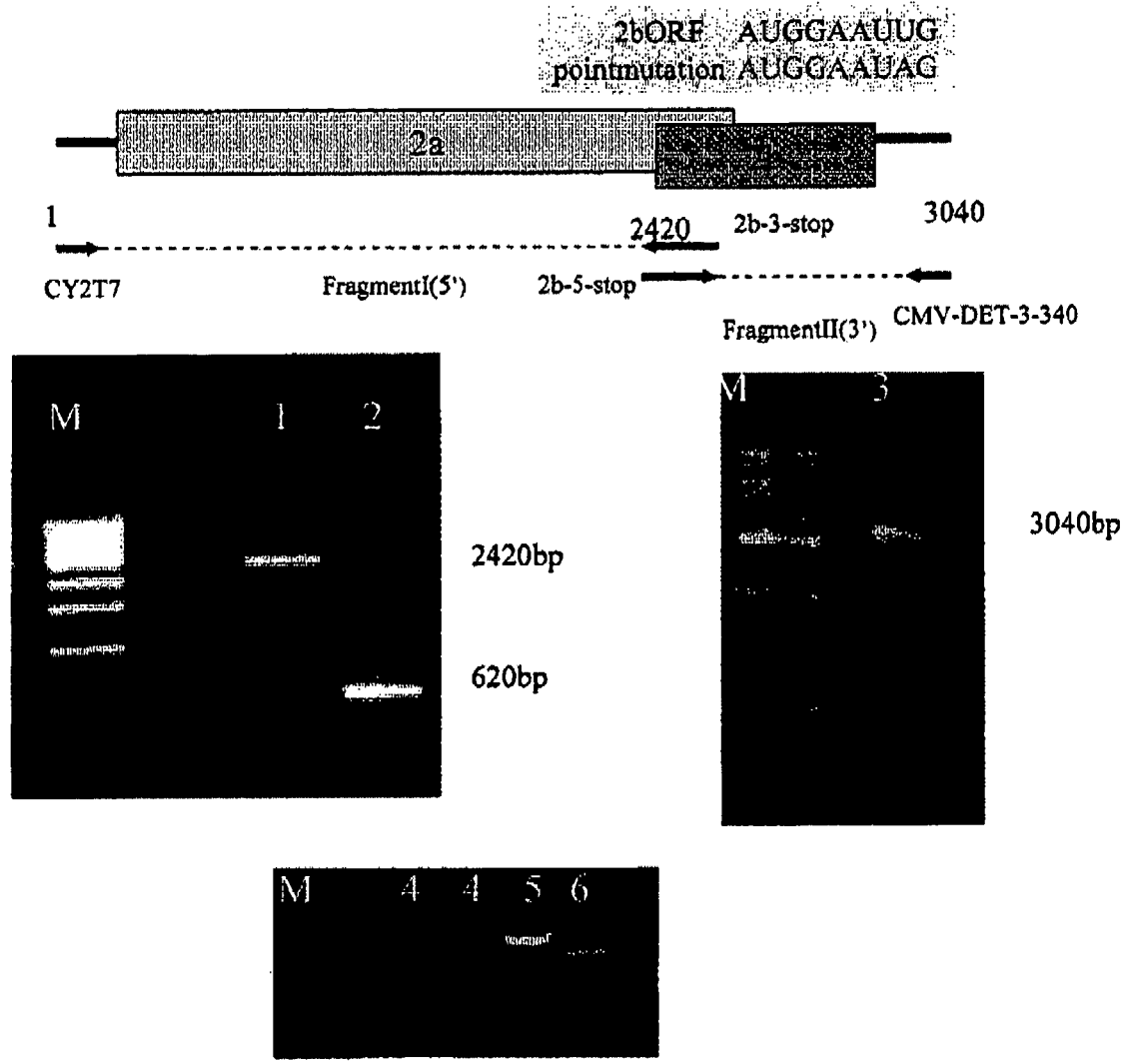
FIG. 2 shows the structure of pCY2-2bstop, and contains the primers CY2T7: CCGGATCCATTAATACGACTCAC-TATAGTTTATTTACAAAGAGCG (SEQ ID NO: 3); 2b-5-stop: AGAAATATGGAATAGAACGTAGG (SEQ ID NO: 4); and 2b-3-stop: CCTACGTTCTATTCCATATTTCT (SEQ ID NO: 5).

In CMV-Y RNA2, the 2b protein is coded for in overlapping fashion with the 2a protein, which forms part of the virus's multiple enzyme complex. Consequently, when introducing a stop codon into the ORF of the 2b protein care must be taken to prevent amino acid substitutions in the 2a protein. To meet this condition, a point mutation is introduced which changes the 8th base of the 2b ORF from U (uracil) to A (adenine). This point mutation causes no amino acid substitutions in the 2a ORF. A strategy for introducing the point mutation is shown in FIG. 2.

That is, the following sense and antisense primers were prepared in the sequence for introducing the point mutation, and subjected to PCR together with the respective 3' and 5' primers to amplify Fragments I (lane 1) and II (lane 2). The respective bands were cut out and mixed, and used as templates in PCR using the 5' and 3' primers (CY2T7, CMV-DET-3-340) (lane 3). When the PCR Fragment of lane 3 was cleaved with HindIII and BlnI (lane 4), a fragment was observed in the same position as pCY2 (lane 5). This band was cut out and cloned into the HindIII-XbaI region of pUC119. The accurate introduction of the point mutation was confirmed by looking at the mutation in the sequence. The HindIII-StuI region was cut out from the pUC119-point mutation, and introduced into the HindIII-StuI region of pCY2. Accurate introduction of the point mutation into the resulting pCY2-2bstop was confirmed by sequencing.

(Primers)

```
CY2T7:
                                        (SEQ ID NO: 3)
CCGGATCCATTAATACGACTCACTATAGTTTATTTACAAAGAGCG;

2b-5-stop:
                                        (SEQ ID NO: 4)
AGAAATATGGAATAGAACGTAGG;

2b-3-stop:
                                        (SEQ ID NO: 5)
CCTACGTTCTATTCCATATTTCT;
```

In an inoculation test together with the transcription products of pCY1 and pCY3, systemic infection occurred in *benthamiana* and *tabacum* but the symptoms progressed more slowly than those of the wild type (Table 5).

(15) Introduction of Foreign Gene GFP into CMV-Y RNA2

Figure 3:
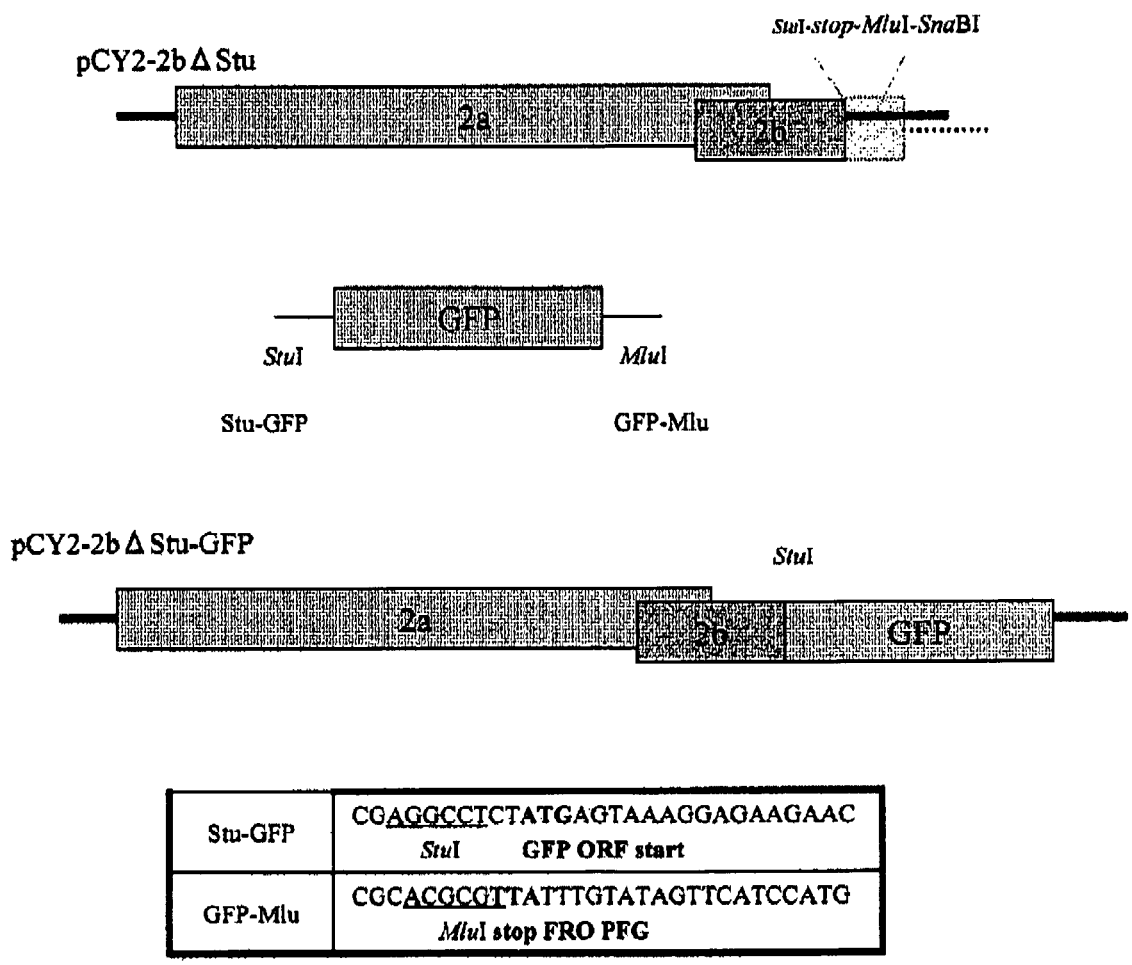
FIG. 3 shows introduction of a foreign gene (GFP) into CMV-YRNA2, and contains the primers Stu-GFP: CGAG-GCCTCTATGAGTAAAGGAGAAGAAC (SEQ ID NO: 6); and GFP-.Mlu: CGCACGCGTTATTTGTATAGTTCATC-CATG (SEQ ID NO: 7).
Figure 4:
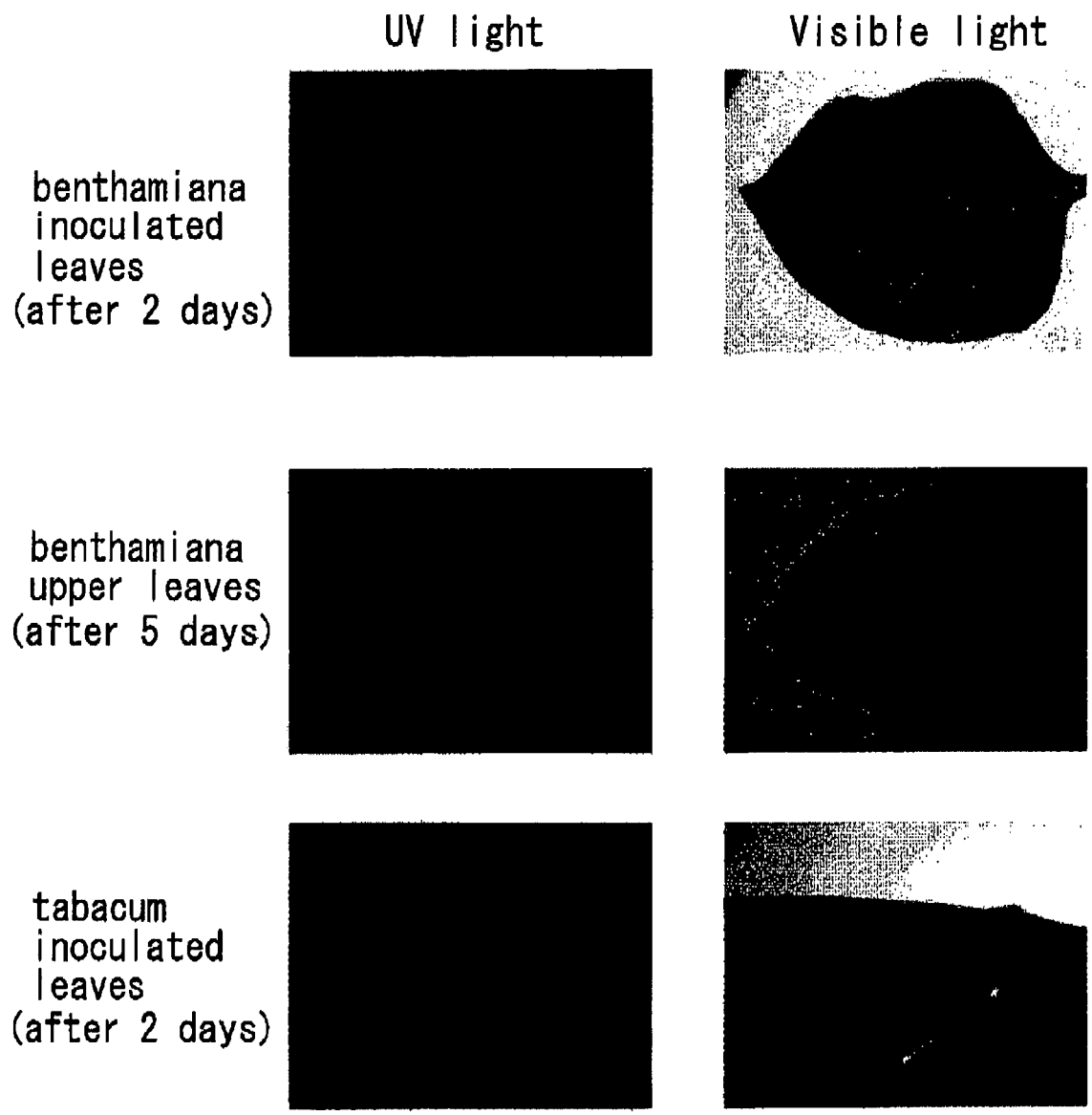
FIG. 4 shows detection of GFP fluorescence from Y1 Y2-GFPY3 (RNA transcription product) in *bentlzamiana* and *tabacum*.

When pCY2-2bΔStu having the CMV-Y 2b protein C-end deleted was transcribed in vitro, mixed with separately transcribed Y1 and Y3 and inoculated, it produced systemic infection in *benthamiana* and *tabacum*. The GFP sequence was therefore inserted into the MluI region and StuI site of pCY2-2bΔStuI with the aim of making pCY2-2bΔStuI into a virus vector through incorporation of foreign DNA into the 2b deletion site. The process of introduction of the foreign gene (GFP) into CMV-Y RNA2 is shown in FIG. 3. PCR was performed using pC3-S65T-GFP as the template to add the StuI site onto the 5' end and the MluI site onto the 3' end of the GFP ORF. Next, the GFP fragment was cloned into the StuI-MluI region of pCY2-2bΔStu to construct pCY2-2bΔStu-GFP. When this pCY2-2bΔStu-GFP plasmid with the inserted GFP sequence was transcribed in vitro and inoculated into *benthamiana* and *tabacum* together with the RNA transcription products of pCY1 and pCY3, GFP fluorescence was observed in inoculated leaves 2 days after inoculation and in upper leaves 5 days after inoculation. Results for detection of GFP fluorescence from Y1Y2-GFPY3 (RNA transcription product) in *benthamiana* and *tabacum* are shown in FIG. 4.

(16) Results

Observation of GFP fluorescence in inoculated leaves 2 days after inoculation and upper leaves 5 days after inoculation revealed GFP fluorescence in the virus infection points of the inoculated leaves, while in the upper leaves extremely strong GFP fluorescence was seen throughout the leaves in the same way as the disease symptoms.

INDUSTRIAL APPLICABILITY

As explained above, the present invention relates to a novel CMV vector with the RNA2 molecule of CMV modified and the like, and a novel plant RNA virus vector is provided by the present invention. This vector produces systemic infection in inoculated plants, and can cause stable expression of foreign genes. Moreover, this vector has at least about 1000 species of host plants in which it can be used as a vector. A novel method of expressing plant genes is provided. This method is useful as a plant gene expression method for introducing foreign genes and causing them to be expressed stably in plants. Replicability thereof is high, and the method is useful for stopping gene expression through gene silencing.

The invention claimed is:

1. A cucumber mosaic virus strain Y (CMV-Y) wherein a region from a StuI site to a stop codon of an ORF encoding 2b protein of RNA2 is deleted and a region from an initiation codon to the StuI site of the ORF encoding 2b protein of RNA2 remains.

2. The CMV-Y vector according to claim 1, further comprising nucleotides 1 to 22 (CGAGGCCTGACGCGTGTACGTA) of SEQ ID NO: 1).

3. A recombinant vector, comprising a cucumber mosaic virus strain Y (CMV-Y) vector wherein a region from a StuI site to a stop codon of an ORF encoding 2b protein of RNA2 is deleted, a region from an initiation codon to the StuI site of the ORF encoding 2b protein of RNA2 remains, and a foreign polynucleotide encoding a protein is introduced into the StuI site.

4. A method of expressing a polynucleotide in a plant comprising introducing the recombinant vector defined in claim 3 in a manner to stably express the protein encoded by the foreign polynucleotide in the plant.

* * * * *

SEQUENCE LISTING

```
<160> NUMBER OF SEQ ID NOS: 7

<210> SEQ ID NO 1
<211> LENGTH: 40
<212> TYPE: DNA
<213> ORGANISM: Artificial
<220> FEATURE:
<223> OTHER INFORMATION: Synthetic DNA

<400> SEQUENCE: 1
cgaggcctga cgcgtgtacg taaacctccc cttccgcatc                    40

<210> SEQ ID NO 2
<211> LENGTH: 27
<212> TYPE: DNA
<213> ORGANISM: Artificial
<220> FEATURE:
<223> OTHER INFORMATION: Synthetic DNA
```

```
<400> SEQUENCE: 2
ccatcgattg gtctcctttt ggaggcc                                              27

<210> SEQ ID NO 3
<211> LENGTH: 45
<212> TYPE: DNA
<213> ORGANISM: Artificial
<220> FEATURE:
<223> OTHER INFORMATION: Synthetic DNA

<400> SEQUENCE: 3
ccggatccat taatacgact cactatagtt tatttacaaa gagcg                          45

<210> SEQ ID NO 4
<211> LENGTH: 23
<212> TYPE: DNA
<213> ORGANISM: Artificial
<220> FEATURE:
<223> OTHER INFORMATION: Synthetic DNA

<400> SEQUENCE: 4
agaaatatgg aatagaacgt agg                                                  23

<210> SEQ ID NO 5
<211> LENGTH: 23
<212> TYPE: DNA
<213> ORGANISM: Artificial
<220> FEATURE:
<223> OTHER INFORMATION: Synthetic DNA

<400> SEQUENCE: 5
cctacgttct attccatatt tct                                                  23

<210> SEQ ID NO 6
<211> LENGTH: 29
<212> TYPE: DNA
<213> ORGANISM: Artificial
<220> FEATURE:
<223> OTHER INFORMATION: Synthetic DNA

<400> SEQUENCE: 6
cgaggcctct atgagtaaag gagaagaac                                            29

<210> SEQ ID NO 7
<211> LENGTH: 30
<212> TYPE: DNA
<213> ORGANISM: Artificial
<220> FEATURE:
<223> OTHER INFORMATION: Synthetic DNA

<400> SEQUENCE: 7
cgcacgcgtt atttgtatag ttcatccatg                                           30
```